United States Patent
Hansen et al.

(10) Patent No.: US 11,931,063 B2
(45) Date of Patent: Mar. 19, 2024

(54) TISSUE-REMOVING CATHETER WITH TORQUE CONTROL

(71) Applicant: Medtronic Vascular, Inc., Santa Rosa, CA (US)

(72) Inventors: Bryan Hansen, Galway (IE); Aram Jamous, Athenry (IE)

(73) Assignee: MEDTRONIC VASCULAR, INC., Santa Rosa, CA (US)

( * ) Notice: Subject to any disclaimer, the term of this patent is extended or adjusted under 35 U.S.C. 154(b) by 42 days.

(21) Appl. No.: 17/651,897

(22) Filed: Feb. 21, 2022

(65) Prior Publication Data
US 2022/0304719 A1 Sep. 29, 2022

Related U.S. Application Data

(60) Provisional application No. 63/266,105, filed on Dec. 28, 2021, provisional application No. 63/165,394, filed on Mar. 24, 2021.

(51) Int. Cl.
*A61B 17/3207* (2006.01)
*A61B 17/00* (2006.01)
*A61B 90/00* (2016.01)

(52) U.S. Cl.
CPC ............ *A61B 17/320758* (2013.01); *A61B 2017/00039* (2013.01); *A61B 2017/00292* (2013.01);
(Continued)

(58) Field of Classification Search
CPC ...... A61B 17/30075; A61B 17/320725; A61B 17/320758; A61B 2017/06;
(Continued)

(56) References Cited

U.S. PATENT DOCUMENTS 4,679,557 A * 7/1987 Opie .............. A61B 17/320758
606/108
7,172,610 B2 2/2007 Heitzmann et al.
(Continued)

FOREIGN PATENT DOCUMENTS

WO WO2000056230 A2 9/2000

OTHER PUBLICATIONS

International Search Report and Written Opinion for PCT/IB2022/052586, dated Aug. 1, 2022, 18 pages, Rijswijk, Netherlands.
(Continued)

*Primary Examiner* — Tuan V Nguyen
(74) *Attorney, Agent, or Firm* — Stinson LLP

(57) ABSTRACT

A tissue-removing catheter for removing tissue in a body lumen includes an elongate body having an axis and proximal and distal end portions spaced apart from one another along the axis. A tissue-removing element is mounted on the distal end portion of the elongate body. The tissue-removing element is configured to remove the tissue as the tissue-removing element is rotated by the elongate body within the body lumen. A motor operatively engages the elongate body for driving rotation of the elongate body and tissue-removing element mounted on the elongate body. A controller is operatively connected to the motor and configured to perform a torque response routine to control a speed of the motor based on a set PWM value of the motor and a detected current applied to the motor during rotation of the elongate body and tissue-removing element.

17 Claims, 14 Drawing Sheets

(52) U.S. Cl.
CPC ............... *A61B 2017/00398* (2013.01); *A61B 2017/0042* (2013.01); *A61B 2090/066* (2016.02)

(58) Field of Classification Search
CPC ......... A61B 2017/00039; A61B 2017/002926; A61B 2017/00398
See application file for complete search history.

(56) References Cited

U.S. PATENT DOCUMENTS

| | | |
|---|---|---|
| 7,959,050 B2 | 6/2011 | Smith et al. |
| 8,142,365 B2 | 3/2012 | Miller |
| 8,382,782 B2 | 2/2013 | Robertson et al. |
| 9,597,110 B2 | 3/2017 | Kesler et al. |
| 10,052,122 B2 | 8/2018 | Higgins et al. |
| 10,251,664 B2 | 4/2019 | Shelton, IV et al. |
| 10,258,364 B2 | 4/2019 | Isakov et al. |
| 10,368,902 B2 | 8/2019 | Kessler et al. |
| 10,588,629 B2 | 3/2020 | Malinouskas et al. |
| 2007/0239182 A1* | 10/2007 | Glines ............ A61B 17/320758 606/159 |
| 2010/0125276 A1* | 5/2010 | Palermo ......... A61B 17/320758 408/1 R |
| 2014/0222042 A1* | 8/2014 | Kessler .......... A61B 17/320758 606/159 |
| 2014/0371770 A1 | 12/2014 | Schoenle et al. |
| 2015/0201956 A1* | 7/2015 | Higgins ......... A61B 17/320725 606/159 |
| 2016/0135831 A1 | 5/2016 | Schimitz et al. |
| 2019/0059980 A1 | 2/2019 | Shelton, IV et al. |
| 2019/0125361 A1 | 5/2019 | Shelton, IV et al. |
| 2019/0200977 A1 | 7/2019 | Shelton, IV et al. |
| 2019/0206565 A1 | 7/2019 | Shelton, IV |
| 2019/0262022 A1 | 8/2019 | Spangler et al. |

OTHER PUBLICATIONS

ME Bertrand et al., Percutaneous Coronary Rotary Ablation, Herz. 15(5):285-91, Oct. 1990, PubMed.
PK Raju et al., High Speed Rotational Atherectomy in Coronary Artery Disease, Surg Technol Int. 2:255-8, Oct. 1993, PubMed.

* cited by examiner

TISSUE-REMOVING CATHETER WITH TORQUE CONTROL

CROSS-REFERENCE TO RELATED APPLICATIONS

This application claims the benefit of U.S. Provisional Patent Application Ser. No. 63/165,394, filed on Mar. 24, 2021, and U.S. Provisional Patent Application Ser. No. 63/266,105, filed on Dec. 28, 2021, the entire contents of each are hereby incorporated by reference.

FIELD

The present disclosure generally relates to a tissue-removing catheter, and more particular, to a tissue-removing catheter having torque control capability.

BACKGROUND

Tissue-removing catheters are used to remove unwanted tissue in body lumens. As an example, atherectomy catheters are used to remove material from a blood vessel to open the blood vessel and improve blood flow through the vessel. This process can be used to prepare lesions within a patient's coronary artery to facilitate percutaneous coronary angioplasty (PTCA) or stent delivery in patients with severely calcified coronary artery lesions. Atherectomy catheters typically employ a rotating element which is used to abrade or otherwise break up the unwanted tissue.

SUMMARY

In one aspect, a tissue-removing catheter for removing tissue in a body lumen generally comprises an elongate body having an axis and proximal and distal end portions spaced apart from one another along the axis. The elongate body is sized and shaped to be received in the body lumen. A tissue-removing element is mounted on the distal end portion of the elongate body. The tissue-removing element is configured to remove the tissue as the tissue-removing element is rotated by the elongate body within the body lumen. A motor operatively engages the elongate body for driving rotation of the elongate body and tissue-removing element mounted on the elongate body. A controller is operatively connected to the motor and configured to perform a torque response routine to control a speed of the motor based on a set PWM value of the motor and a detected current applied to the motor during rotation of the elongate body and tissue-removing element.

In another aspect, a tissue-removing catheter for removing tissue in a body lumen generally comprises an elongate body having an axis and proximal and distal end portions spaced apart from one another along the axis. The elongate body is sized and shaped to be received in the body lumen. A tissue-removing element is mounted on the distal end portion of the elongate body. The tissue-removing element is configured to remove the tissue as the tissue-removing element is rotated by the elongate body within the body lumen. A motor operatively engages the elongate body for driving rotation of the elongate body and tissue-removing element mounted on the elongate body. A controller is operatively connected to the motor and configured to monitor a speed of the motor. The controller deactivates the motor in response to a change in the monitored speed being greater than a predetermined amount for a predetermined period of time.

In yet another aspect, a tissue-removing catheter for removing tissue in a body lumen generally comprises an elongate body having an axis and proximal and distal end portions spaced apart from one another along the axis. The elongate body is sized and shaped to be received in the body lumen. A tissue-removing element is mounted on the distal end portion of the elongate body. The tissue-removing element is configured to remove the tissue as the tissue-removing element is rotated by the elongate body within the body lumen. A motor assembly includes a motor and a motor drivetrain output. The motor assembly operatively engages the elongate body for driving rotation of the elongate body and tissue-removing element mounted on the elongate body. A controller is operatively connected to the motor and configured to control a speed of the motor. The controller controls the speed of the motor based on a logistic speed control curve.

BRIEF DESCRIPTION OF THE DRAWINGS

Corresponding reference characters indicate corresponding parts throughout the drawings.

DETAILED DESCRIPTION

Figure 1:
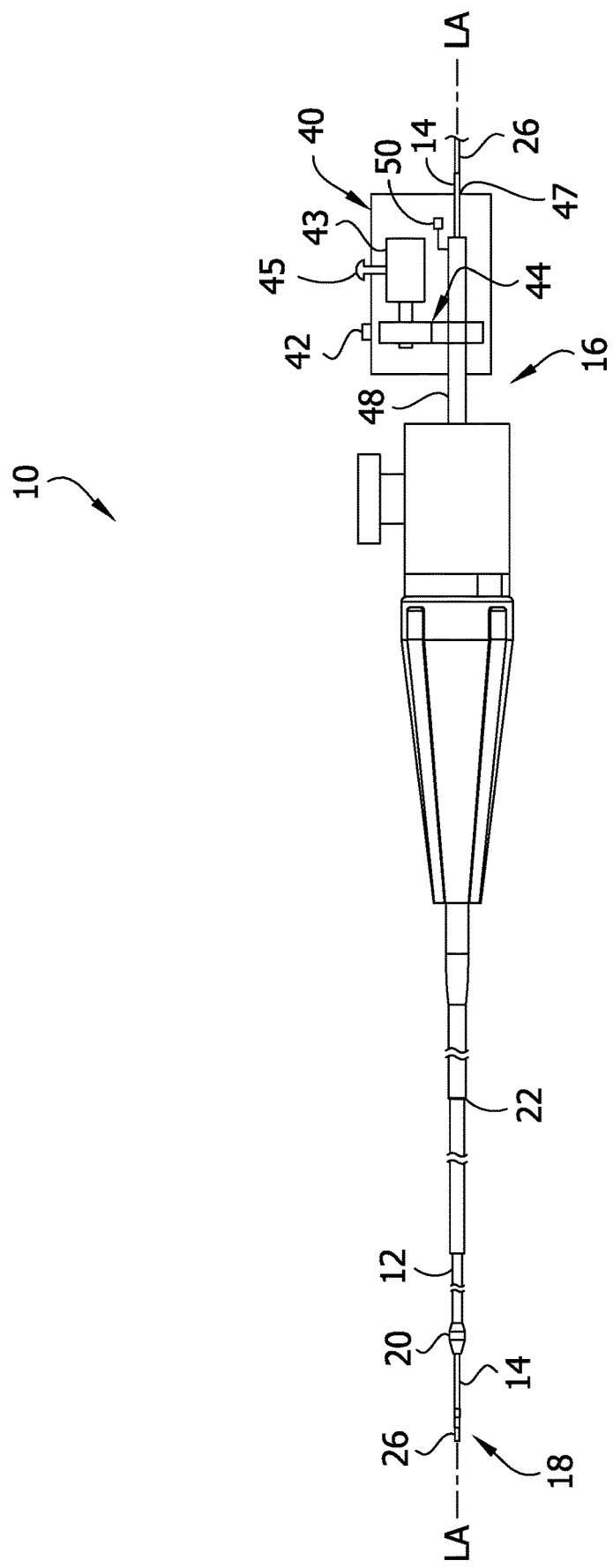
FIG. 1 is a schematic elevation of a catheter of the present disclosure.

Referring to the drawings, and in particular FIG. 1, a rotational tissue-removing catheter for removing tissue in a body lumen is generally indicated at reference number 10. The illustrated catheter 10 is a rotational atherectomy device suitable for removing (e.g., abrading, cutting, excising, ablating, etc.) occlusive tissue (e.g., embolic tissue, plaque tissue, atheroma, thrombolytic tissue, stenotic tissue, hyperplastic tissue, neoplastic tissue, etc.) from a vessel wall (e.g., coronary arterial wall, etc.). The catheter 10 may be used to facilitate percutaneous coronary angioplasty (PTCA) or the subsequent delivery of a stent. Features of the disclosed embodiments may also be suitable for treating chronic total occlusion (CTO) of blood vessels, and stenoses of other body lumens and other hyperplastic and neoplastic conditions in other body lumens, such as the ureter, the biliary duct, respiratory passages, the pancreatic duct, the lymphatic duct, and the like. Neoplastic cell growth will often occur as a result of a tumor surrounding and intruding into a body lumen. Removal of such material can thus be beneficial to maintain patency of the body lumen.

The catheter 10 is sized for being received in a blood vessel of a subject. Thus, the catheter 10 may have a maximum size of 3, 4, 5, 6, 7, 8, 9, 10, or 12 French (1, 1.3, 1.7, 2, 2.3, 2.7, 3, 3.3, or 4 mm) and may have a working length of 20, 30, 40, 60, 80, 100, 120, 150, 180 or 210 cm depending of the body lumen. While the remaining discussion is directed toward a catheter for removing tissue in blood vessels, it will be appreciated that the teachings of the present disclosure also apply to other types of tissue-removing catheters, including, but not limited to, catheters for penetrating and/or removing tissue from a variety of occlusive, stenotic, or hyperplastic material in a variety of body lumens.

Figure 2:
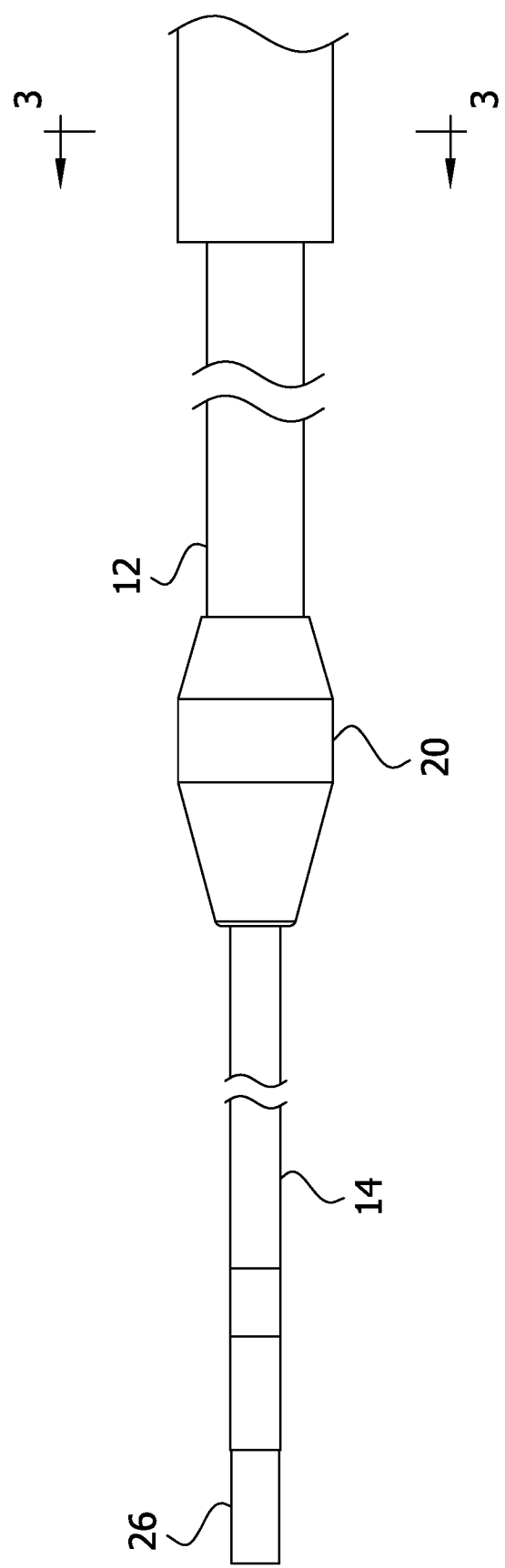
FIG. 2 is an enlarged elevation of a distal end portion of the catheter.
Figure 3:
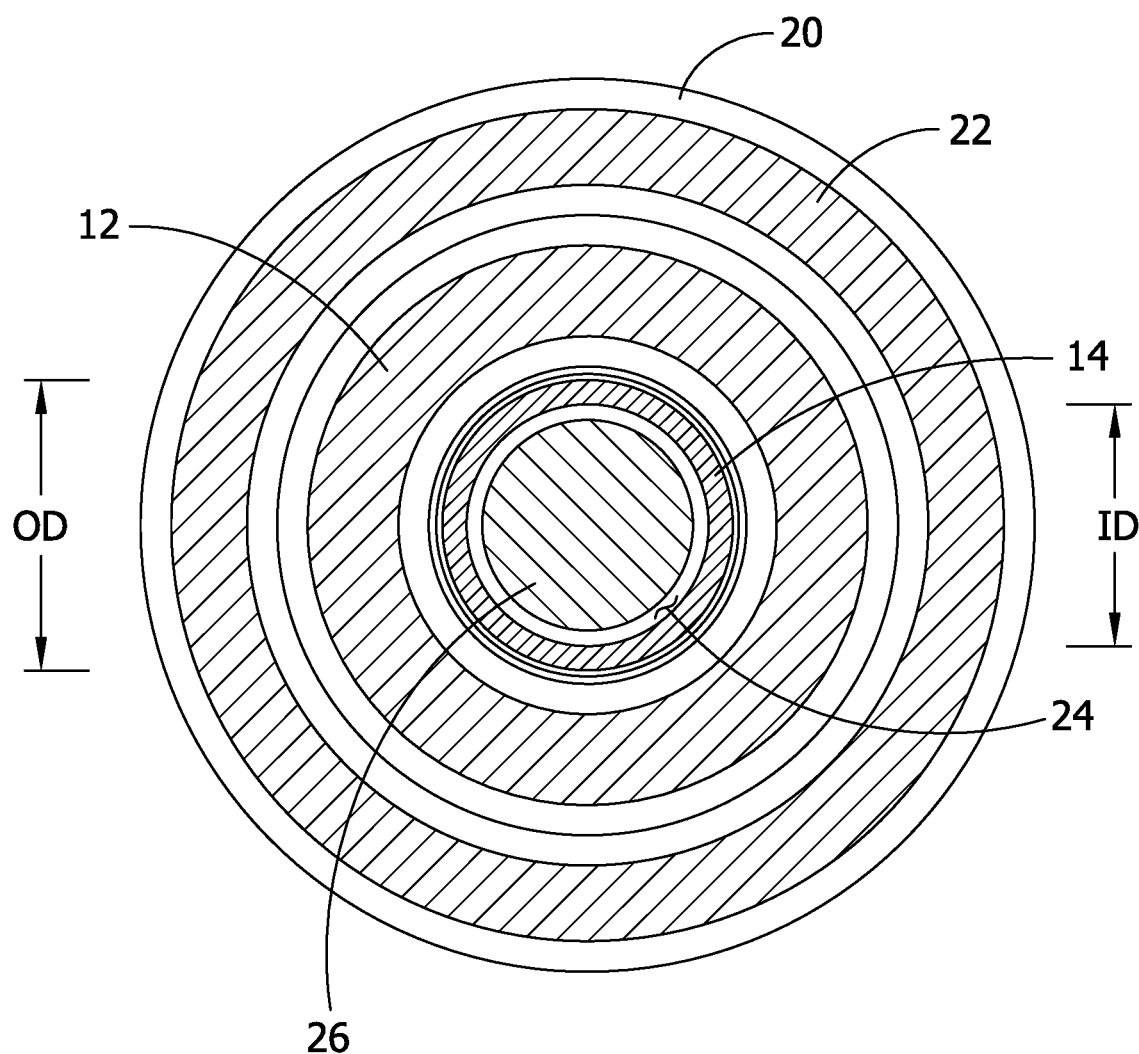
FIG. 3 is a cross section taken through line 3-3 in FIG. 2.

Referring to FIGS. 1-3, the catheter 10 comprises an elongate outer layer or drive coil 12 (broadly, an elongate body) disposed around an elongate inner liner 14. The outer layer 12 and inner liner 14 extend along a longitudinal axis LA of the catheter from a proximal end portion 16 to a distal end portion 18 of the catheter. A tissue-removing element 20 is disposed on a distal end of the outer layer 12 and is configured for rotation to remove tissue from a body lumen as will be explained in greater detail below. A sheath 22 (FIG. 1) is disposed around the outer layer 12. The outer layer 12 and the inner liner 14 are both configured to translate relative to the sheath 22. The outer layer 12 and inner liner 14 are also configured to translate relative to each other. The catheter 10 is sized and shaped for insertion into a body lumen of a subject. The sheath 22 isolates the body lumen from at least a portion of the outer layer 12 and inner liner 14. The inner liner 14 defines a guidewire lumen 24 for slidably receiving a guidewire 26 therein so that the catheter 10 can be advanced through the body lumen by traveling along the guidewire. The guidewire can be a standard 0.014-inch outer diameter, 300 cm length guidewire. In certain embodiments, the inner liner 14 may have a lubricious inner surface for sliding over the guidewire 26 (e.g., a lubricious surface may be provided by a lubricious polymer layer or a lubricious coating). In the illustrated embodiment, the guidewire lumen 24 extends from the proximal end portion 16 through the distal end portion 18 of the catheter 10 such that the guidewire 26 is extendable along an entire working length of the catheter 10. In one embodiment, the overall working length of the catheter 10 may be between about 135 cm (53 inches) and about 142 cm (56 inches). In use, the guidewire 26 may extend about 40 mm (1.6 inches) past a distal end of the inner liner 14.

Figure 4:
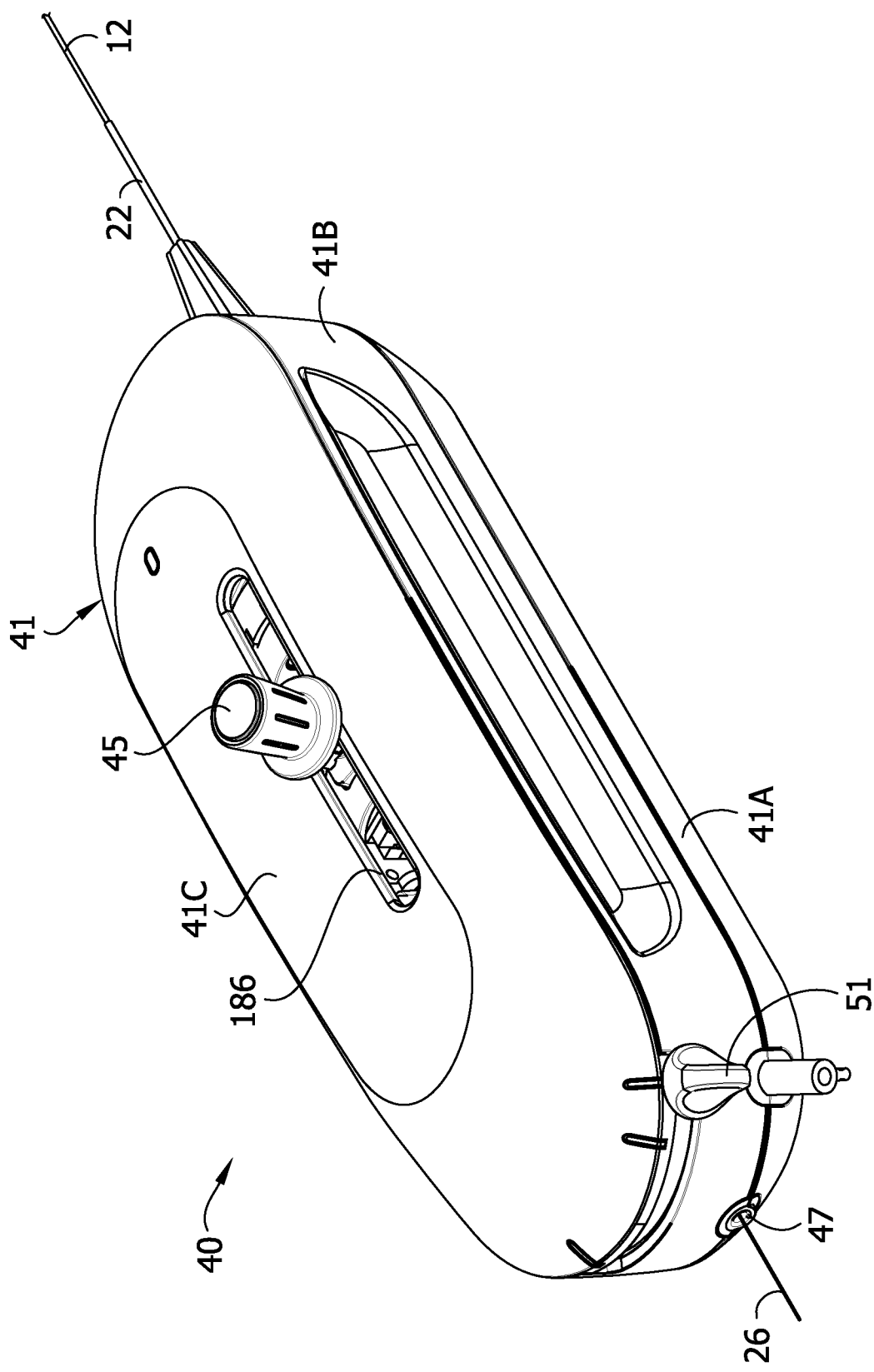
FIG. 4 is a top perspective of a handle of the catheter.
Figure 5:
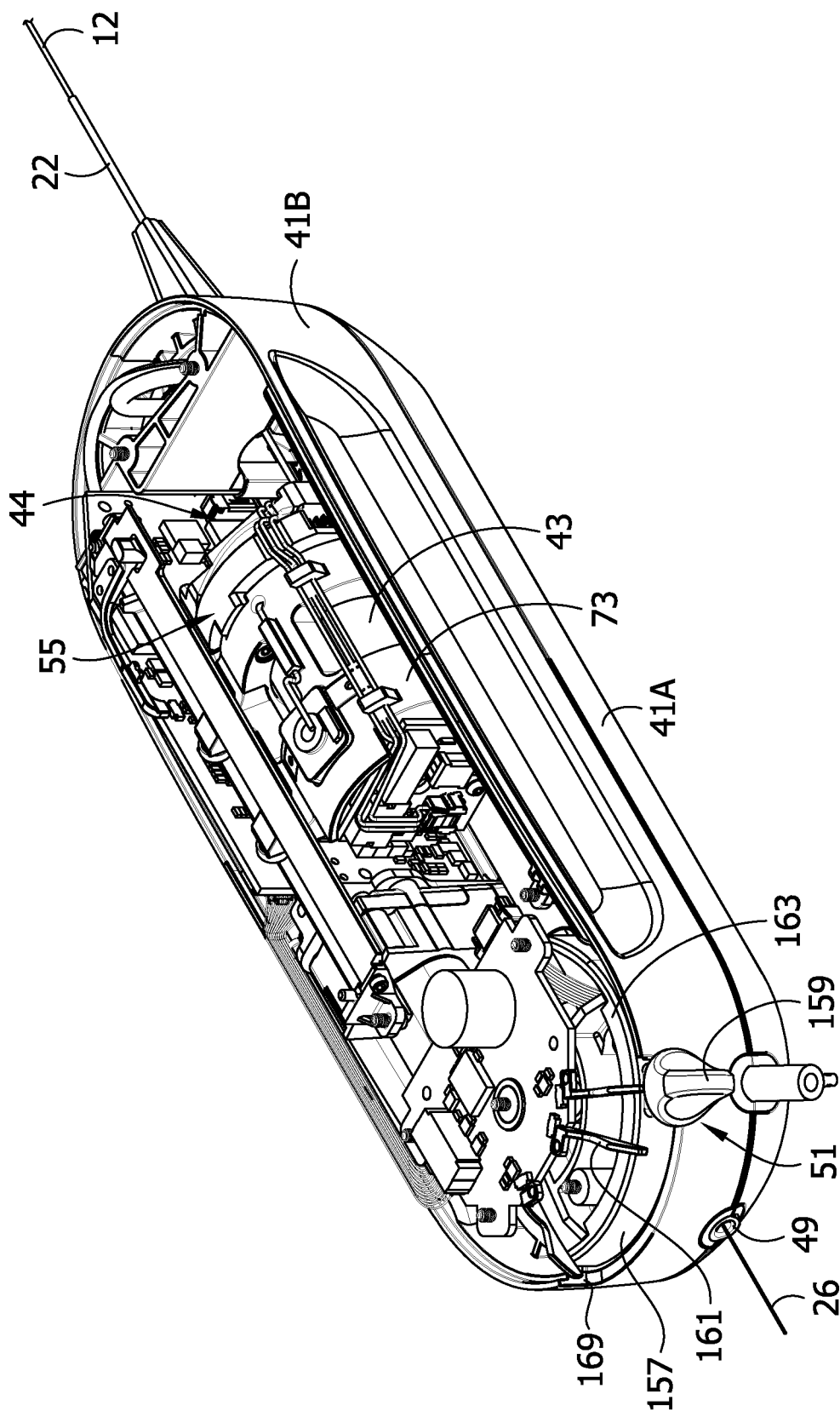
FIG. 5 is a top perspective of the handle with a top housing section removed.
Figure 6:
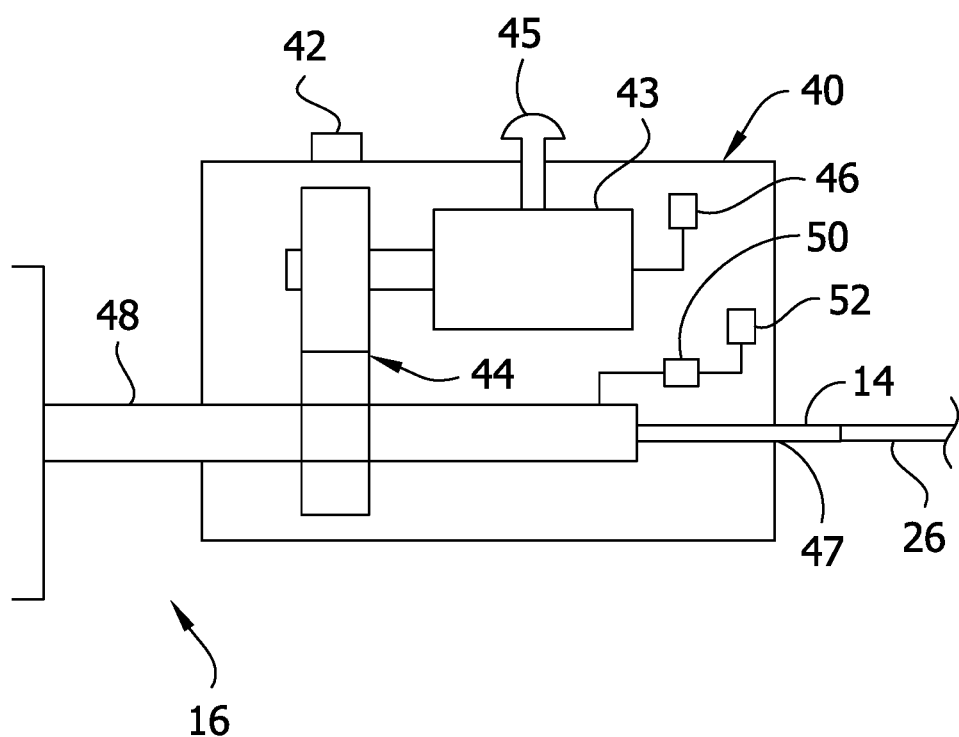
FIG. 6 is an enlarged schematic elevation of a proximal end portion of the catheter.

Referring to FIGS. 4-6, the catheter 10 further comprises a handle 40 secured at a proximal end of the isolation sheath 22. The handle 40 comprises a housing 41 that supports the components of the handle. The housing 41 has a generally elongate egg shape and includes as plurality of housing sections secured together to enclose the internal components of the handle 40. In the illustrated embodiment, the housing 41 includes a bottom housing section 41A, a middle housing section 41B secured to the top of the bottom housing section, and a top housing section 41C secured to the top of the middle housing section. It will be understood that the housing 41 can have other shapes and configurations without departing from the scope of the disclosure.

The housing 41 supports an actuator 42 (e.g., a lever, a button, a dial, a switch, or other device) configured for selectively actuating a motor 43 disposed in the handle to drive rotation of the outer layer or drive coil 12, and tissue-removing element 20 mounted at the distal end of the drive coil. The motor 43 is configured to rotate the drive coil 12 and tissue-removing element 20 at speeds of up to about 100,000 RPM. The motor 43 is coupled to the drive coil 12 by a gear assembly 44 and drive assembly 48 (broadly, a motor drivetrain output) supported within the housing 41. Thus, when current is applied to the motor 43 from a power source, the electrical energy from the current is converted into mechanical energy to rotate the drive assembly 48 for rotating the outer layer 12. Further, the speed of the motor 43 may be controlled by pulse width modulation (PWM). Therefore, through the use of PWM, the speed of the motor 43 can be varied which increases the efficiency of the motor and allows the catheter to control the torque in the system, as will be explained in greater detail below. A sensor (e.g., optical sensor) 46 may also be provided in the handle 40 and operatively connected to the motor 43 to measure the rotational speed of the motor. Other methods for measuring the speed of the motor 43 may be incorporated without departing from the scope of the disclosure. In some embodiments, deactivation of the motor 43 can be caused by actuating the actuator 42 when the motor has been previously actuated.

Additionally, a mode selector 51 may be mounted generally between the middle housing section 41B and the top housing section 41C and define a portion of the housing 41. The mode selector 51 can be configured to selectively place the catheter 10 in a plurality of different modes of operation. Once the mode selector 51 is operated to place the catheter 10 within a particular mode, actuation of the actuator 42 may cause the catheter to begin operation or start the process for operating the catheter 10, and in particular the motor 43, in the selected mode. As will be further explained, operation of the motor 43 may be controlled differently depending on the mode in which the catheter is operating.

Figure 7:
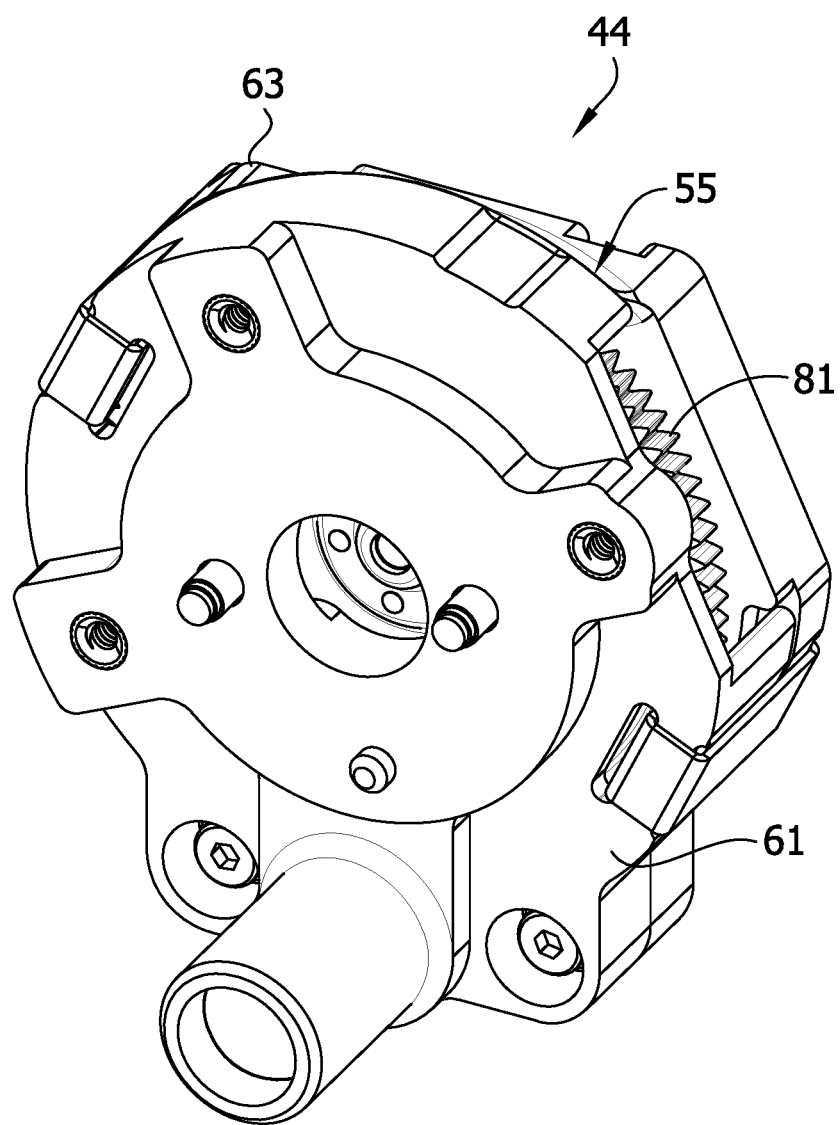
FIG. 7 is a perspective of a gear assembly in the handle.
Figure 8:
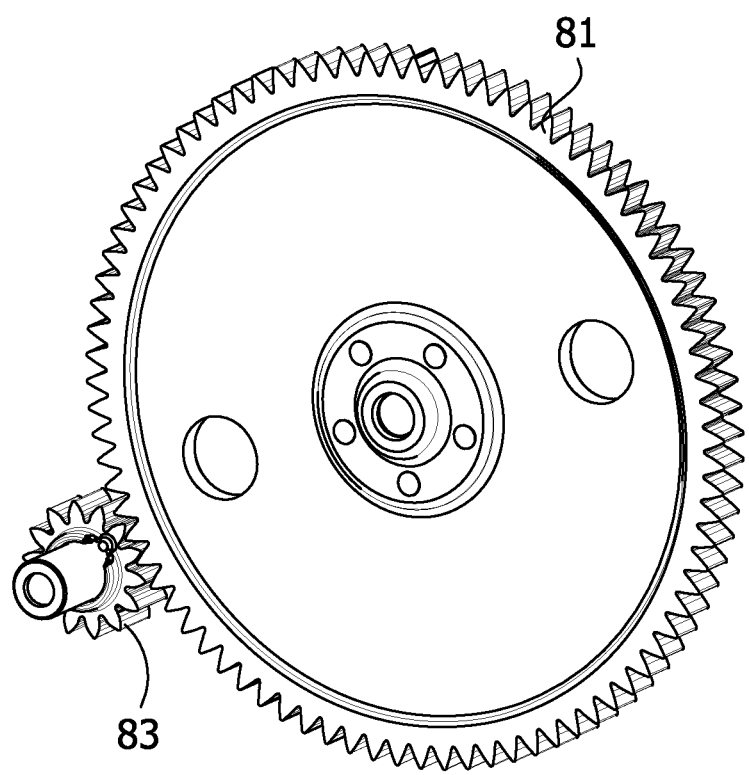
FIG. 8 is a perspective of gears of the gear assembly.

Referring to FIGS. 5, 7, and 8, the gear assembly 44 comprises a gearbox housing 55 that mounts and at least partially encloses a pair of gears for transferring the rotation of a shaft of the motor 43 to the drive coil 12. The gearbox housing 55 includes a main housing section 61 and a front housing section 63. The main housing section 61 attaches to a carriage or advancer frame 73 for moving the motor 43 and gear assembly 44 within the housing 41. Further, attaching the gearbox housing 55 to the distal end of the advancer frame 73 secures the motor 43 in the advancer frame so that the motor moves along with the advancer frame. A driven gear 83 is in mesh with the driver gear 81 so that rotation of the driver gear causes the driven gear to rotate in the opposite direction. The drive assembly 48 attaches the driven gear 83 to the drive coil 12 so that the rotation of the driven gear causes the drive coil to rotate.

Referring to FIGS. 4-6, a slide or advancer 45 is positioned on the handle 40 and is operatively coupled to the outer layer 12 for movement of the outer layer relative to the handle to advance and retract the outer layer and tissue-removing element 20. The handle 40 defines a slot 186 which limits the movement of the slide 45 relative to the handle. Thus, the length of the slot 186 determines the amount of relative movement between the outer layer 12 and the handle 40. In one embodiment, the slot 186 has a length of about 70 mm (2.8 inches). A proximal port 47 allows for passage of the guidewire 26 through the proximal end of the handle 40. A guidewire lock 49 may be provided in the handle 40 to lock the guidewire 26 in place relative to the handle. In one embodiment, the guidewire lock 49 engages the guidewire 26 to lock the guidewire in place when the mode selector 51 is moved to place the catheter 10 in a mode for abrasion.

It is understood that other suitable actuators, including but not limited to touchscreen actuators, wireless control actuators, automated actuators directed by a controller, etc., may be suitable to selectively actuate the motor in other embodiments. In some embodiments, a power supply may come from a battery (not shown) contained within the handle 40. The battery can provide the current source for the guidewire detection circuit. In other embodiments, the power supply may come from an external source.

Referring to FIG. 6, a controller 50 is provided in the handle 40. The controller 50 may be programmed to detect the current being applied to the motor 43 for rotating the motor and drive assembly 48. In one embodiment, the current is continuously monitored so as to control the amount of torque being applied at the drive assembly 48. In particular, motor current along with the motor drive PWM duty cycle is used to estimate the torque at the tissue-removing element 20. This allows the catheter 10 to prevent an over-torqueing condition where the torque experienced at the tissue-removing element 20 exceeds a predetermined limit which may cause damage to the motor or the surrounding tissue. As will be explained in greater detail below, the controller 50 is configured to perform a series of motor control operations for controlling the speed of the motor 43 in response to an estimated torque at the drive assembly 48. The controller 50 may also deactivate the motor 43 if the rotational speed falls below a predetermined amount. For instance, if a rotational speed of less than 15,000 RPM is detected, the motor 43 may be deactivated. Additionally, if the change in speed (i.e., deceleration) of the motor 43 exceeds a predetermined rate, the motor 43 may be deactivated. In one embodiment, motor rotation is halted by active or dynamic braking. Dynamic braking occurs by "crowbarring" the motor 43 to rapidly dissipate the kinetic energy of the motor as heat and electrical energy through a resistive load.

The controller 50 may be configured to produce an alarm signal (e.g., audible sound, visual indication, etc.) and/or prevent or halt rotation of the motor 43 when an error condition is determined. For example, it the estimated torque at the drive assembly 48 exceeds a predetermined amount or when motor speed drops below a preset limit, the controller 50 may deactivate the motor 43 to stop rotation of the tissue-removing element. In one embodiment, the controller 50 is configured to deactivate the motor 43 upon a detected motor speed of less than 85,000 RPM. The catheter 10 may be calibrated to determine the estimated torque at the drive assembly 48 based on measuring the motor current required at a given load at different motor drive PWM levels. Thus, for a known load or torque, the catheter 10 can be calibrated to determine the motor output that will be produced in response to that load. Therefore, by measuring the motor current and tracking the PWM level during use, the catheter 10 can estimate the amount of torque the catheter is experiencing by referencing the calibration data. For example, a calibration table including a plurality of known loads/torques and the expected motor output response can be stored in the catheter memory 52 for use by the controller 50.

Referring to FIGS. 4 and 5, the mode selector 51 may comprise a guide portion 157 that is supported by the housing 41, a lever 159 attached to the guide portion and actuatable to move the guide portion relative to the housing, and a motor switching portion 161 operatively connected to the guide portion for causing the motor 43 to change its operational state based on the position of the guide portion. In the illustrated embodiment, the guide portion 157 sits on a floor 163 of the middle housing section 41B and pivots relative to the middle housing section. Other engagements between the mode selector 51 and the housing 41 that facilitate the same or other forms of movement of the mode selector are also envisioned. For example, the mode selector could be integrated with the actuator 42 such that sequential presses of the actuator cycle through the modes of the catheter 10. Still other configurations are envisioned.

In one embodiment, the controller 50 is configured to operate the motor 43 in a "standby mode" where the motor is deactivated and the guidewire 26 is unlocked so that the guidewire can be moved relative to the catheter 10. In the "standby mode" the catheter 10 may be configured to ignore input from the actuator 42. Thus, the motor 43 cannot be activated in "standby mode." However, if the catheter 10 is currently operating in a mode that causes rotation of the motor 43, placing the motor in the "standby mode" may deactivate the motor to cease motor rotation.

Figure 9:
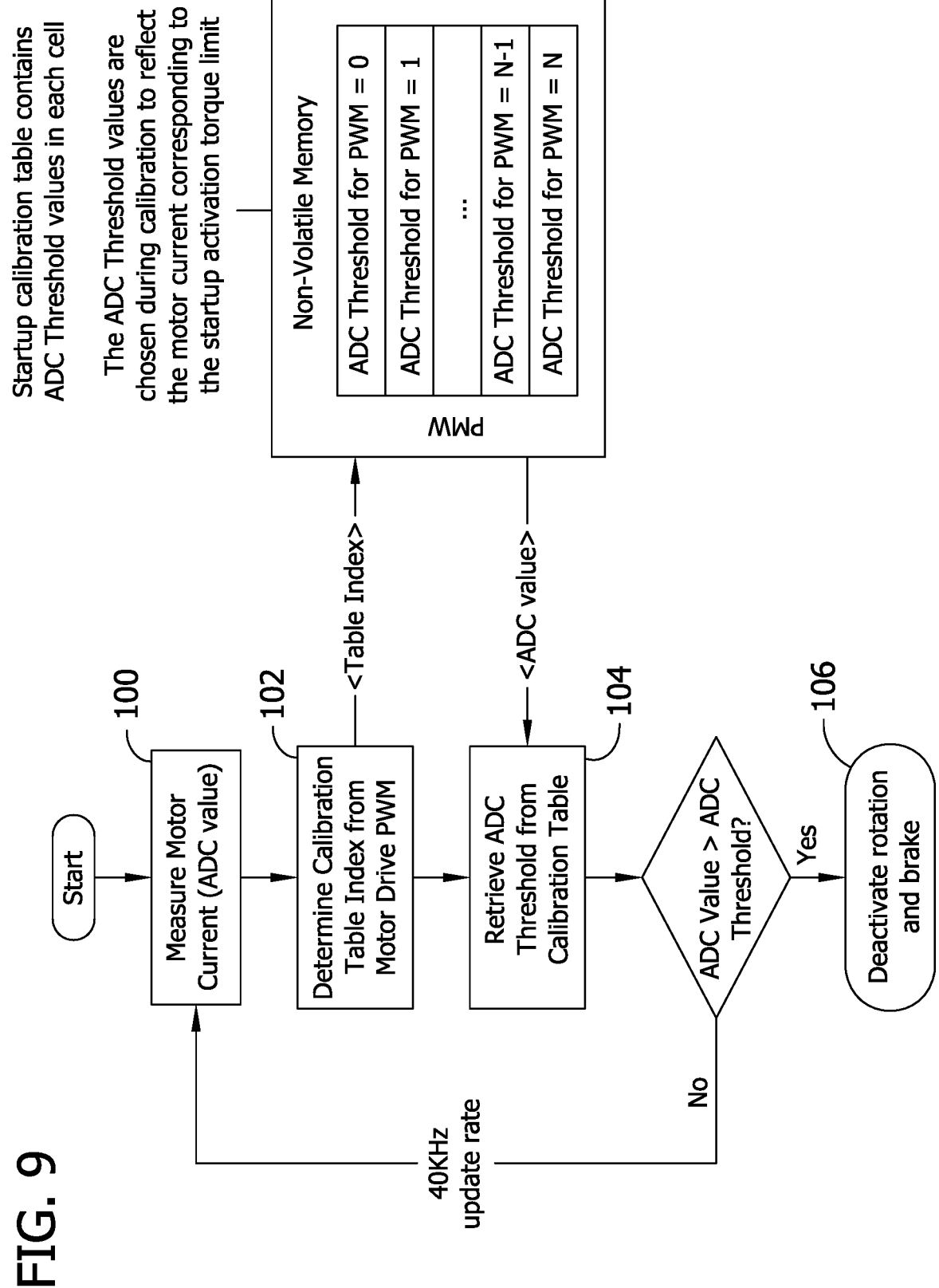
FIG. 9 is a flow chart of a start-up mode torque control routine of the catheter.

The lever 159 is actuatable to place the motor 43 in either a "track mode" or an "ablation mode." At the start of either mode, the controller 50 is configured to run a "start-up mode" routine where the motor is activated to begin rotation of the tissue-removing element 20. Referring to FIG. 9, during the "start-up mode" routine the controller 50 may be programmed to control operation of the motor 43 in response to the estimated torque at the drive assembly 48. For example, the controller 50 may implement a torque response routine where motor current is monitored using a 1-dimensional lookup table. The procedure provides a direct correlation between motor current and estimated torque at the drive assembly 48. A "start-up mode" routine lookup table may be stored in the catheter memory 52 which provides estimated torque values for a given motor current value. Using this lookup table, a torque control routine can be performed. In particular, the torque control routine is performed where at 100, the motor current is sampled to receive an ADC value. The current motor drive PWM is also known at the time of sampling. Then at 102, a calibration table index is determined from the motor drive PWM value and motor current measurement. A motor current threshold value is then retrieved from the lookup table at 104. If the motor current value is above the threshold the motor 43 is deactivated at 106. Alternatively, if the motor current value is less than the threshold, the process is repeated at a preset time interval to continuously control the motor 43 during the "start-up mode" routine. In one embodiment, the routine is repeated every 25 microseconds (40 kHz). However, the routine could be performed at other update rates without departing from the scope of the disclosure. In one embodiment, the "start-up mode" routine functions to protect the catheter 10 and surrounding anatomy during use if the catheter is unable to freely rotate or is otherwise entrapped or damaged. The controller 50 may operate in the "start-up mode" until the motor speed reaches a threshold of about 35,000 RPM. However, the threshold may be otherwise set without departing from the scope of the disclosure.

At the completion of the "start-up mode" routine, when the lever 159 is actuated to place the motor 43 in the "track mode," the motor is activated to produce a first output and the guidewire 26 is kept unlocked. The first motor output may be a reduced output which generates a pulsed output and/or a relatively slow rotation of the drive coil 12. In one embodiment, the motor 43 rotates at least about 5,000 RPM and less than about 30,000 RPM in the "track mode". The "track mode" may be initiated when the catheter 10 is navigating through a particularly tortuous passage. In the illustrated embodiment, the "track mode" is initiated by pivoting the lever 159 to an intermediate position between the stops 169. After initiation of the "track mode" the controller 50 may operate the motor 43 at a fixed PWM value to achieve a motor speed of about 10,000 RPM. The fixed PWM value may be determined during calibration of the catheter 10. Referring to FIG. 9, the controller 50 may also be programmed to limit an estimated torque at the drive assembly 48 to less than or equal to a predetermined amount while the motor 43 is being increased to an operating "track mode" speed. In one embodiment, the controller 50 compares the motor current to a threshold value to control the torque being applied to the catheter 10. The controller 50 may deactivate the motor 43 if the estimated torque exceeds the threshold value. In an alternative embodiment, the catheter 10 implements a one-factor lookup procedure whereby the controller 50 monitors motor current to estimate the torque at the drive assembly 48. A "track mode" lookup table may be stored in the catheter memory 52 which provides estimated torque values for a given motor current. The controller 50 may deactivate the motor 43 if the estimated torque exceeds the predetermined amount before the motor reaches the "track mode" operating speed. In one embodiment, the controller 50 is configured to deactivate the motor 43 if the estimated torque exceeds about 1.1 mNm. Once the operating speed for "track mode" is reached, the catheter 10 may indicate that it is in "track mode".

Figure 10:
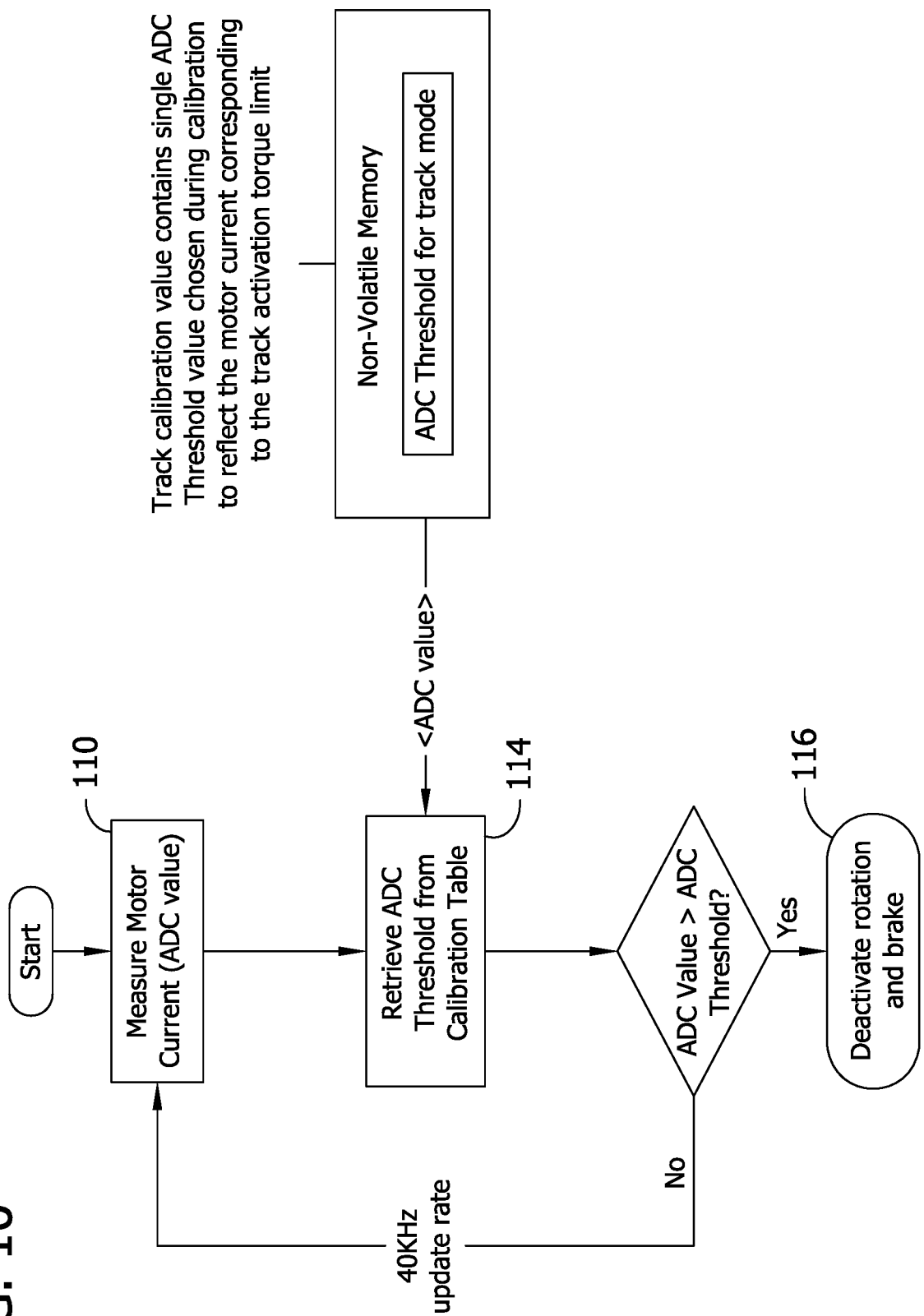
FIG. 10 is a flow chart of a track mode torque control routine of the catheter.

Referring to FIG. 10, in "track mode" the controller 50 may be programmed to control operation of the motor 43 in response to the estimated torque at the drive assembly 48. For example, the controller 50 my implement a torque response routine during "track mode" where motor current is monitored using a current threshold value stored in the memory 52. Thus, the procedure provides a direct correlation between motor current and the estimated torque at the drive assembly 48. In particular, the "track mode" torque control routine is performed where at 110, the motor current is sampled to receive an ADC value. A motor current threshold value is then retrieved from the memory 52 at 114. If the motor current value is above the threshold the motor 43 is deactivated at 116. Alternatively, if the motor current value is less than the threshold, the process is repeated at a preset time interval to continuously control the motor 43 during the "track mode." In one embodiment, the routine is repeated every 25 microseconds (40 kHz). However, the routine could be performed at other update rates without departing from the scope of the disclosure.

Figure 11:
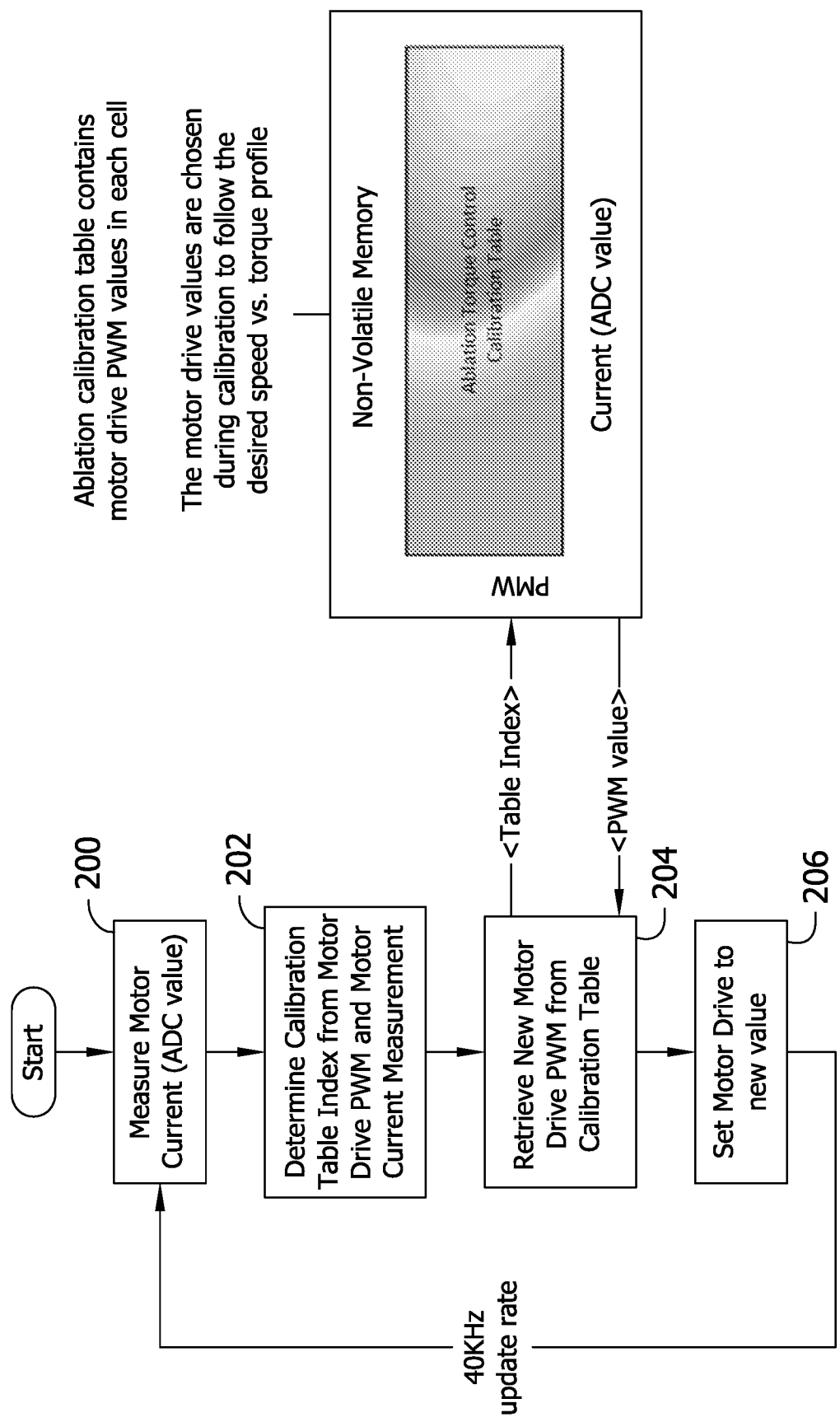
FIG. 11 is a flow chart of an ablation mode torque control routine of the catheter.

Referring to FIGS. 5 and 11, at the completion of the "start-up mode" routine, when the lever 159 is actuated to place the motor 43 in the "ablation mode," the motor is activated to produce a second output and the guidewire 26 is locked relative to the catheter 10. The second motor output may be an operational output which is increased over the first output so that a relatively high-speed rotation of the drive coil 12 is achieved. In one embodiment, the motor 43 produces a rotation of about 100,000 RPMs in the "ablation mode." In one embodiment, the motor 43 produces a rotation of at least about 15,000 RPM in "ablation mode." The "ablation mode" may be initiated when the catheter 10 is operating to remove occlusive tissue from a vessel wall. Thus, ablation torque control must be able to respond to resistance encountered during ablation and limit the maximum torque applied by the catheter 10. During high speed rotation, kinetic energy is stored in the rotating components of the catheter 10 including the motor 43, gear assembly 44, bearing races, catheter coil 12 and interfaces, and the tissue-removing element 20. Controlling the torque at the drive assembly 48 can be done by reducing the motor voltage, however, the stored kinetic energy must be dissipated. This is done through actively braking the motor 43.

In one embodiment, the "ablation mode" is initiated by pivoting the lever 159 to engage the other of the stops 169 on the housing 41. Movement of the lever 159 to this position will also cause a locking pin (not shown) to press against the guidewire 26 locking the guidewire in place. After initiation of the "ablation mode" the controller 50 may be programmed to limit an estimated torque at the drive assembly 48 to less than or equal to a predetermined amount while the motor 43 is being increased to a minimum operating "ablation mode" speed. In one embodiment, the minimum operating "ablation mode" speed is about 20,000 RPM. The controller 50 may deactivate the motor 43 if the estimated torque exceeds the predetermined amount before the motor reaches the "ablation mode" minimum operating speed. In one embodiment, the controller 50 is configured to deactivate the motor 43 if the estimated torque exceeds about 1.1 mNm. In one embodiment, the catheter 10 indicates that it is in "ablation mode" immediately upon initiation of "ablation mode." Alternatively, once the minimum operating speed for "ablation mode" is reached, the catheter 10 may indicate that it is in "ablation mode".

In the "ablation mode" the controller 50 may be programmed to control operation of the motor 43 in response to the estimated torque at the drive assembly 48. For example, the controller 50 may implement a torque response routine during ablation where the motor drive PWM duty cycle is set using a 2-dimensional lookup table based on motor current measurements and input PWM duty cycle values to output new PWM duty cycles which in turn control the speed of the motor 43 thereby controlling the torque at the tissue-removing catheter. In one embodiment, during operation in the "ablation mode," the catheter 10 implements a two-factor lookup procedure whereby the controller 50 monitors the motor current and existing PWM values to new motor drive PWM duty cycle values to estimate the torque at the drive assembly 48. The procedure provides a direct correlation between motor drive PWM and motor current with an estimated torque at the drive assembly 48. An "ablation mode" lookup table may be stored in the catheter memory 52 at manufacturing which provides estimated torque values for a given motor current value and motor drive PWM value pair. In particular, the lookup table is populated with motor drive PWM values and motor current values which correspond to an estimated torque value. Using this lookup table, an "ablation mode" torque control routine can be performed. In one embodiment, the controller 50 initiates the torque control routine once the motor 43 reaches the minimum operating "ablation mode" speed.

Referring to FIG. 11, the torque control routine is performed where at 200, the motor current is sampled to receive an ADC value. The current motor drive PWM is also known at the time of sampling. Then at 202, a calibration table index is determined from the motor drive PWM and motor current measurements. From the calibration table index, a new motor drive PWM value is selected by referencing the lookup table at 204. The lookup table provides a new motor drive value that corresponds to the measured motor current and input PWM value, and the new PWM value is applied at 206. This process is repeated at a preset time interval to continuously control the motor 43 during ablation. In one embodiment, the routine is repeated every 25 microseconds (40 kHz). It will be understood that the routine could be repeated at other time intervals without departing from the scope of the disclosure.

Figure 12:
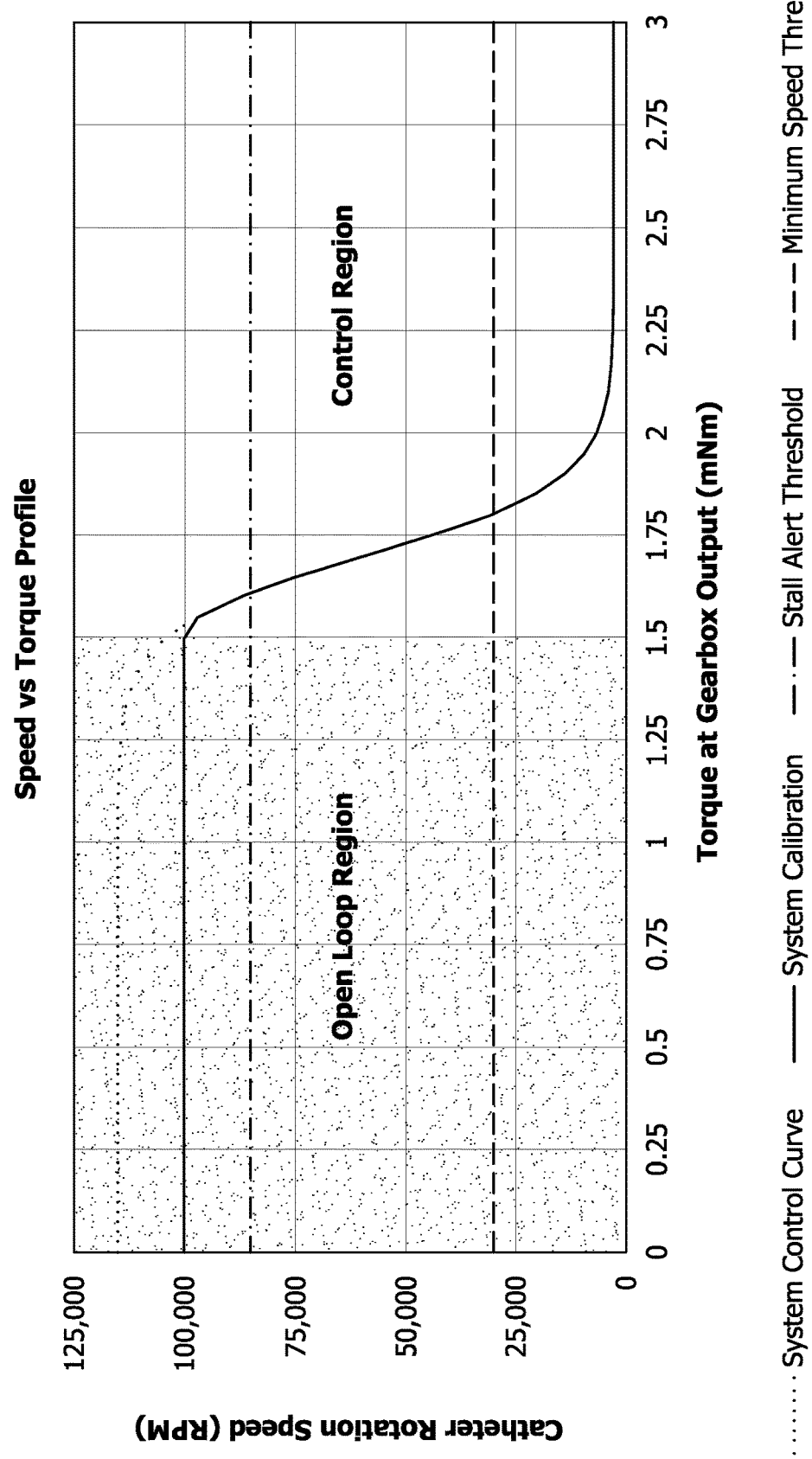
FIG. 12 is a graph of a speed control profile used by the catheter.

The PWM values populated in the lookup table correspond to a desired speed along a control profile (FIG. 12). Thus, the new PWM values change the speed of the motor 43 in response to the estimated torque which was determined based on the measured motor current and input motor drive PWM values. The control profile in FIG. 12 includes an Open Loop section and a Control Region section. In one embodiment, the Open Loop section includes estimated torque levels of less than about 1.5 mNm. The profile is populated with the motor drive PWM values from a calibration where the motor 43 rotates generally at a constant rate. In the illustrated embodiment, the motor 43 rotates at about 100,000 RPM. In the Open Loop section, the motor 43 is allowed to change speeds (i.e., decelerate/accelerate) based on the characteristic of the motor and drive train at a constant motor PWM drive duty cycle. The Open Loop section contains estimated torque values consistent with the tissue-removing element 20 receiving little to no impedance to rotation. Thus, the control profile is set to rotate the motor at the optimal motor rotation speed. In one embodiment, the Control Region section includes estimated torque values of about 1.5 mNm and above. In one embodiment, the Control Region section includes estimated torque values of from about 1.5 mNm to about 3 mNm. In the Control Region section, the lookup table is populated with calibrated motor PWM values to follow the desired speed profile for each estimated torque value. Thus, the estimated torques rise to the level of requiring some degree of correction to prevent the torque from increasing to a dangerous level. Therefore, when a new motor PWM drive value is applied, the motor 43 changes its speed to match the adjusted speed target indicated in the Control Region section. During ablation, the motor 43 may also be automatically deactivated if the motor speed drops below about 30,000 RPM. In one embodiment, this minimum speed threshold defines the maximum torque capability in normal use.

In general, the controller 50 can be configured to detect changes in speed of the motor 43 as an early indication of an increasing torque at the tissue-removing element 20 which is likely to result in an over-torqueing condition. For instance, in the "ablation mode" when the motor 43 is rotating at a rate of greater than about 15,000 RPM, if the motor rotation speed decreases a sufficient amount over a predetermined period of time, the controller 50 may deactivate the motor 43 to prevent an over-torqueing condition from occurring. In one embodiment, the controller 50 samples speed measurements at a preset interval (e.g., every 1 ms) over a period of time (e.g., 32 ms). The change in speed between consecutive speed measurements is calculated. Finally, a sum of the calculated change in speed measurements is performed to determine a total sum of the change in speeds. If the total sum of the calculated change (i.e., decrease) in speeds is above a predetermined threshold, the controller 50 may deactivate the motor 43. Alternatively, the controller 50 may measure a change in speed over a period of time and deactivate the motor 43 if the amount of the change in speed exceeds a predetermined threshold. In yet another embodiment, the controller 50 may deactivate the motor 43 if an 8% or greater decrease in motor speed is detected between two consecutive speed measurements. The speed measurements may be taken in intervals of 25 microseconds. Other speed measurement intervals may also be used. Additionally, the thresholds may be fixed or proportional. As discussed above, the motor 43 may be dynamically braked to dissipate the stored kinetic energy in the motor as heat and electromagnetic forces.

The controller 50 may be configured to instruct an alarm to signal in the result of a detected error condition. For example, if a non-recoverable error is detected, the controller 50 may activate a non-recoverable error alert. In one embodiment, the non-recoverable error alert is provided by an audio alarm and/or a visual LED indicator. The non-recoverable error alert may pre-empt any other active alert. Additionally, the controller 50 may activate a stall alert when the speed of the motor drops to or below about 75,000 RPM. The stall alert may be deactivated once the motor speed reaches or rises above about 80,000 RPM. The stall alert may be provided by an audio alarm. The audio alarm tone sequence may repeat until the stall alert is deactivated. If a lower priority alert is active when the stall alert is activated the controller 50 may wait for the active alert to complete before instructing the stall alert indication be provided. Further, during ablation, the catheter 10 may accumulate an elapsed time since activation and if the elapsed time is equal to or exceeds a predetermined amount (e.g., 30 seconds), then the controller 50 may activate an ablation time alert. The ablation time alert may be provided by an audio indication. If a higher priority alert is active when the ablation time alert is activated, the ablation time alert may be suppressed. Once there are no active higher priority alerts, the ablation time alert can be initiated. Other alarm conditions may also be implemented without departing from the scope of the disclosure.

In order to account for device-to-device variations, a calibration process may be performed to ensure accurate performance of the speed and torque control routines taking into account the slight production variations of each catheter. As such, the calibration process is used to populate the lookup tables used for the torque control procedures performed by the catheter 10 during operation. The calibration process uniquely configures the catheter 10 by calculating the mechanical torque delivered to the catheter as a quadratic function of motor voltage and motor current. The catheter speed is also calculated as a quadratic function of motor voltage and the measured torque load on the system. The calibration process is initiated by measuring motor current and speed values in response to a series of motor drive PWM torque load combinations. In particular, speed contributions of the catheter 10 are modeled using a quadratic transfer function for the change in speed as a function of motor drive PWM and torque load. The transfer functions assume the catheter 10 is in compression since the in use conditions of the catheter primarily place the catheter in compression and the overestimation of torque in the compression state provides an over-torqueing buffer built into the calibration.

The speed control curve is used as an input for the calibration process to produce the lookup tables that are stored in the memory 52 of the catheter 10. The speed control curve may comprise a logistic curve that determines the desired speed for a given torque load. In one embodiment, the logistic curve may be as follows:

$$RPM = \left(\Theta_1 + \frac{\Theta_2 - \Theta_1}{1 + e^{\left(\frac{T-\Theta_3}{\Theta_4}\right)}}\right)(1000)$$

where T is the estimated torque at the drive assembly 48 and the four $\Theta$ coefficients are predetermined calibration values. In one embodiment, $\theta_1 = -3$ (low speed), $\theta_2 = 115$ (calculated speed for 0.5 mNm (high speed)), $\theta_3 = 1.7$ (torque for mid-point speed), and $\theta_4 = 0.09$ (torque curve mid ramp).

Thus, a desired motor speed (RPM) can be calculated from the estimated torque load on the catheter 10. Further, the desired torque limit for "start-up" and "track mode", and the target speed for "track mode" are additional inputs to the calibration process.

Figure 13:
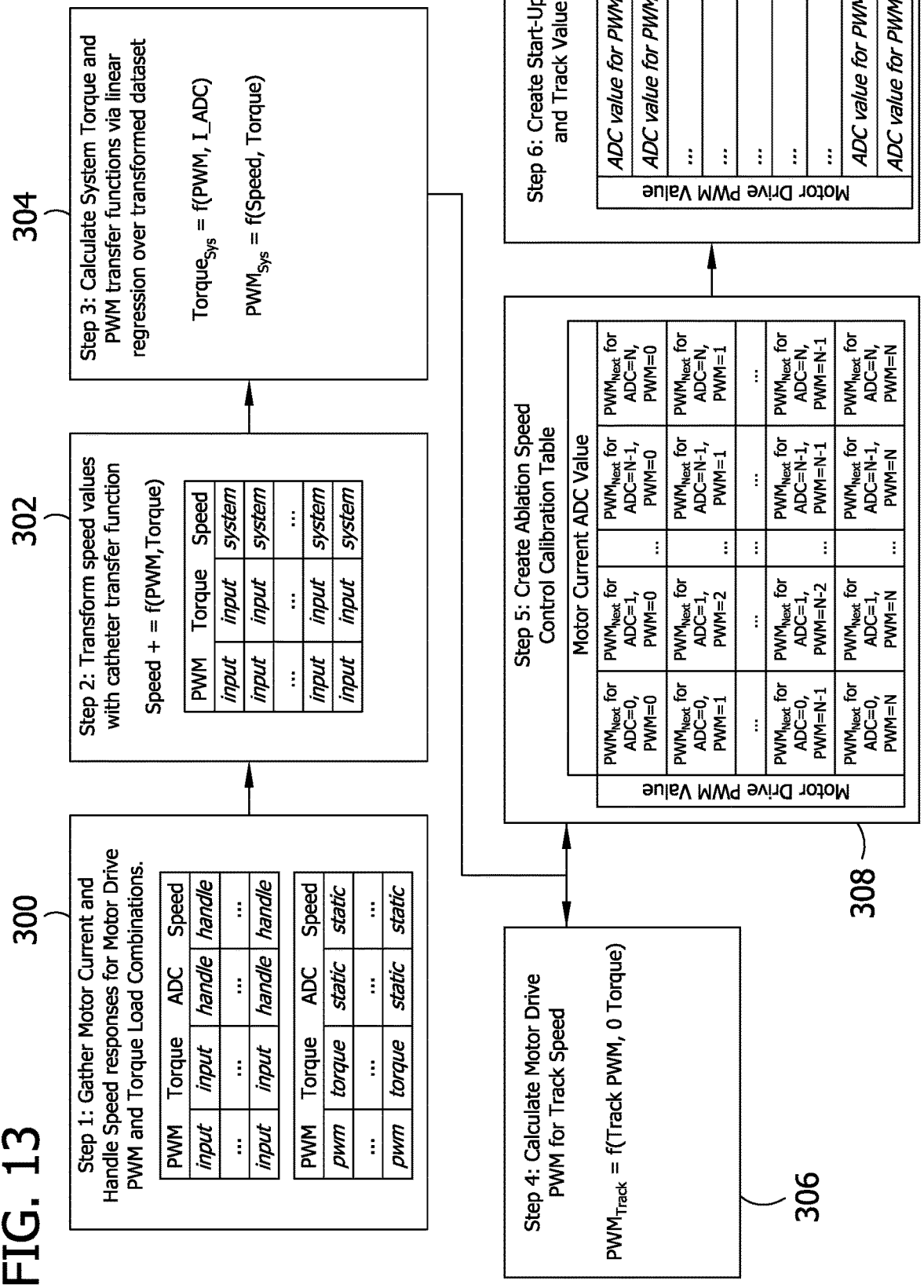
FIG. 13 is an illustration of a calibration process of the present disclosure.

Referring to FIG. 13, separate calibration datasets are created for start-up, track, and ablation torque estimation. The catheter calibration process begins at 300 by gathering motor current and speed values at predetermined motor drive PWM values when the catheter 10 is subject to known torque loads. In particular, during the manufacturing process, a specialized torque application system (TAS) and a manufacturing handle FPGA configuration may be utilized to set the motor drive PWM while applying the known torque loads to generate a data set of measured motor current and speed responses. Because the overall catheter speed and torque at the drive assembly 48 are affected by energy losses throughout the catheter 10, to accurately measure these parameters, motor current and speed are modeled using two quadratic transfer functions. Thus, catheter transfer functions are applied to the motor current and speed values to transform the values at 302. System torque and PWM transfer functions are then calculated at 304 using linear regression over the transformed data set produced at 302. Next, a "track mode" motor drive PWM is calculated at 306. Then at 308 an "ablation mode" speed control calibration table is created, and finally a "start-up" calibration table and "track mode" threshold value is created at 310.

During step 300 of gathering motor current and speed values, the manufacturing calibration test system is used with the manufacturing handle FPGA configuration to set the handle to specific motor drive PWM duty cycles and apply a series of known torque loads to the drive assembly 48. The controller 50 reports motor current measurements and speed values for each motor drive and torque load combination to the calibration system which are held by the calibration system and used to generate the final lookup table outputs. In one embodiment, motor current values are reported in counts [0-4095] which represents a range of 0-2.034 A, and motor speed is reported in counts [0-4095] which represents a range of 0-131,071 RPM. Other ranges for motor current and speed may be used without departing from the scope of the disclosure. The number and specific PWM and torque values may be defined in the manufacturing calibration test system configuration. In one embodiment, the system may be calibrated based on 4 PWM levels and 7 torque levels repeated 3 times for a total of 84 samples in the handle calibration dataset. Other numbers and PWM and torque values may be used without departing from the scope of the disclosure. At 302 the catheter current and speed transfer functions are applied to transform the handle calibration dataset produced at 300 to a system calibration dataset by accounting for the additional motor current and reduced speed contributed by the catheter 10 at each PWM/torque calibration point. At 304, the transformed system calibration dataset is used as input to create two quadratic linear regression models specific to the catheter being calibrated. The first quadratic function pertains to system torque as a function of PWM and motor current. The system torque function may be as follows:

$$Torque_{sys} = (C1*PWM) + (C2*ADC) + (C3*PWM2) + (C4*ADC2) + (C5*PWM*ADC) + C6;$$

and the System PWM as a function of speed and torque may be as follows:

$$PWM_{sys} = (C1*Speed) + (C2*Torque) + (C3*Speed2) + (C4*Torque2) + (C5*Speed*Torque) + C6.$$

Thresholds for allowable regression model error (S) and goodness-of-fit (R2) can be enforced by the calibration test system to prevent excessive error in the calibration. In one embodiment, two separate transfer functions are created for "track mode" and "ablation mode."

At 306 the system PWM transfer function is utilized to calculate the motor drive PWM required to achieve the desired track speed at zero torque load. The calibrated PWM duty cycle is unique for each catheter and can be stored in the memory 52 in the handle 40 as part of the calibration procedure.

Both the system torque and system PWM transfer functions used at 304 are utilized along with the desired ablation speed control curve to create the ablation speed control calibration table at 308. The table is constructed by populating each cell based on a motor drive PWM and motor current combination. In particular, the system torque transfer function is used to calculate the estimated torque represented by the PWM/motor current combination. The desired speed from the ablation speed control curve is calculated for the estimated torque. The system PWM transfer function is then used to calculate the motor drive PWM required to achieve the desired speed, and the resulting PWM value is stored in the ablation speed control calibration table cell corresponding to the PWM/motor current combination.

Finally, at 310 the system torque transfer function is used to create the "start-up" calibration table and "track mode" threshold value. The "start-up" calibration table is constructed by populating each cell based on each motor drive PWM value. In particular, the estimated torque is calculated from the system torque transfer function at the PWM/motor current combination and the resulting motor current value representing the desired torque threshold is stored in the start-up calibration table cell corresponding the PWM value. A single value is stored for the "track mode" data set to operate as the threshold value for better controlling torque at slow rotation speeds.

Figure 14:
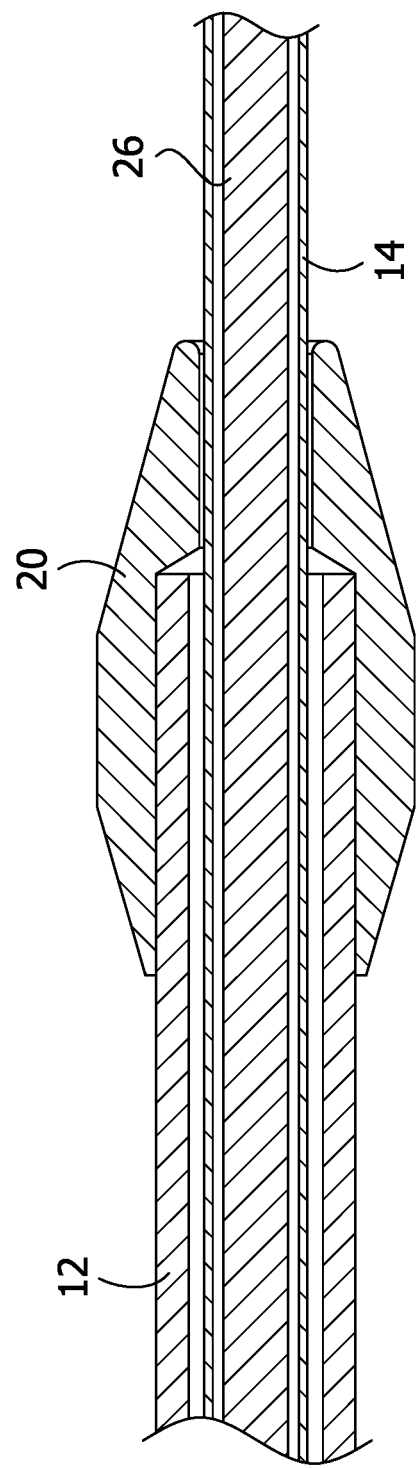
FIG. 14 is an enlarged fragmentary longitudinal cross section of the distal end portion of the catheter in FIG. 2.

Referring to FIGS. 3 and 14, the outer layer 12 may comprise a tubular stainless steel coil configured to transfer rotation and torque from the motor 43 to the tissue-removing element 20. Configuring the outer layer 12 as a coiled structure provides the outer layer with a flexibility that facilitates delivery of the catheter 10 through the body lumen. Also, the coil configuration allows for the rotation and torque of the outer layer 12 to be applied to the tissue-removing element 20 when the catheter 10 is traversed across a curved path. The stiffness of the outer layer 12 also impacts the ease at which the coil is traversed through the body lumen as well as the coil's ability to effectively transfer torque to the tissue-removing element 20. In one embodiment, the outer layer 12 is relatively stiff such that axial compression and extension of the coil is minimized during movement of the catheter 10 through a body lumen. The coil configuration of the outer layer 12 is also configured to expand its inner diameter when the coil is rotated so that the outer layer remains spaced from the inner liner 14 during operation of the catheter 10. In one embodiment, the outer layer 12 has an inner diameter of about 0.023 inches (0.6 mm) and an outer diameter of about 0.035 inches (0.9 mm). In one embodiment, the outer layer 12 has a single layer construction. However, the outer layer 12 may have a multilayer construction.

Referring to FIGS. 3 and 14, the inner liner 14 comprises a multiple layer tubular body configured to isolate the guidewire 26 from the outer layer 12 and tissue-removing element 20. The inner liner 14 is extendable through the handle 40 from a position proximal of the handle to a position distal of the handle. In one embodiment, the inner liner 14 is coupled to the handle 40 but is not fixedly attached to the handle 40 to allow translation of the inner liner relative to the handle. In this embodiment, rotation of the inner liner 14 is not prevented. However, the clearance between the inner liner 14 and the outer layer 12 prevents any rotation of the inner liner caused by the rotation of the outer layer. In this embodiment, both the inner liner 14 and outer layer 12 are permitted to translate relative to the handle 40. Allowing this co-translation of the inner liner 14 and outer layer 12 minimizes compression and extension of the coiled outer layer 14 when force is applied to the outer layer to move the outer layer within the body lumen.

The inner liner 14 has an inner diameter that is sized to pass the guidewire 26. The inner liner 14 protects the guidewire from being damaged by the rotation of the outer layer 12 by isolating the guidewire from the rotatable outer layer. The inner liner 14 also extends past the tissue-removing element 20 to protect the guidewire 26 from the rotating tissue-removing element. Thus, the inner liner 14 is configured to prevent any contact between the guidewire 26 and the rotating components of the catheter 10. Therefore, any metal-to-metal engagement is eliminated by the inner liner 14. This isolation of the outer layer 12 and tissue-removing element 20 from the guidewire 26 also ensures that the rotation of the outer layer and tissue-removing element is not transferred or transmitted to the guidewire. As a result, a standard guidewire 26 can be used with the catheter 10 because the guidewire does not have to be configured to withstand the torsional effects of the rotating components. Additionally, by extending through the tissue-removing element 20 and past the distal end of the tissue-removing element, the inner liner 14 stabilizes the tissue-removing element by providing a centering axis for rotation of the tissue-removing element about the inner liner.

In one embodiment, the inner liner 14 has an inner diameter ID of about 0.016 inches (0.4 mm), an outer diameter OD of about 0.019 inches (0.5 mm), and a length of about 59 inches (1500 mm). The inner diameter ID of the inner liner 14 provides clearance for the standard 0.014-inch guidewire 26. The outer diameter OD of the inner liner 14 provides clearance for the outer layer 12 and tissue-removing element 20. Having a space between the inner liner 14 and the outer layer 12 reduces friction between the two components as well as allows for saline perfusion between the components.

Ideally, the inner liner 14 is disposed around a portion of the guidewire 26 such that the guidewire extends distally from the inner liner. This ensures that the entire length of the catheter 10 is supported by the guidewire 26 so that the catheter can be properly and safely navigated through the body. Also, with the guidewire 26 extending through the distal end of the inner liner 14, the tissue removing element 20 will be properly supported for rotation by the guidewire.

Referring to FIGS. 3 and 14, the tissue-removing element 20 extends along the longitudinal axis LA from a proximal end adjacent the distal end portion of the outer layer 12 to an opposite distal end. The tissue-removing element 20 is operatively connected to the motor 43 for being rotated by the motor. When the catheter 10 is inserted into the body lumen and the motor 43 is rotating the tissue-removing element 20, the tissue-removing element is configured to remove occlusive tissue in the body lumen to separate the tissue from the wall of the body lumen. Any suitable tissue-removing element for removing tissue in the body lumen as it is rotated may be used in one or more embodiments. In one embodiment, the tissue-removing element 20 comprises an abrasive burr configured to abrade tissue in the body lumen when the motor 43 rotates the abrasive burr. The abrasive burr 20 may have an abrasive outer surface formed, for example, by a diamond grit coating, surface etching, or the like. In one embodiment, the tissue-removing element 20 comprises a stainless steel spheroid body with an exterior surface including 5 µm of exposed diamond crystals. The tissue-removing element 20 may also be radiopaque to allow the tissue-removing element to be visible under fluoroscopy. In other embodiments, the tissue-removing element can comprise one or more cutting elements having smooth or serrated cutting edges, a macerator, a thrombectomy wire, etc.

Referring to FIGS. 1 and 2, to remove tissue in the body lumen of a subject, a practitioner inserts the guidewire 26 into the body lumen of the subject, to a location distal of the tissue that is to be removed. Subsequently, the practitioner inserts the proximal end portion of the guidewire 26 through the guidewire lumen 24 of the inner liner 14 and through the handle 40 so that the guidewire extends through the proximal port 47 in the handle. With the catheter 10 loaded onto the guidewire 26, the practitioner advances the catheter along the guidewire until the tissue-removing element 20 is positioned proximal and adjacent the tissue. Initially, the catheter 10 may be placed in the "standby" mode through actuation of the mode selector 51. In this mode, the motor 43 is deactivated and the guidewire 26 is unlocked so that the catheter 10 can be moved relative to the guidewire. As the catheter 10 is being traversed through the body, the mode selector 51 can be moved to the "track mode" where the motor 43 is activated to produce the first output and the guidewire 26 is kept unlocked. The slow rotation of the tissue-removing element 20 at the first output of the motor 43 may be advantageous in navigating the catheter 10 through tortuous pathways. When the tissue-removing element 20 is positioned proximal and adjacent the tissue, the mode selector 51 can be operated to place the catheter 10 in the "ablation mode" to operate the motor 43 at the second output to rotate the drive coil 12 and the tissue-removing element mounted on the drive coil at a higher rate for use in abrading (or otherwise removing) the tissue in the body lumen. This will also lock the guidewire 26 in place. While the tissue-removing element 20 is rotating, the practitioner may selectively move the drive coil 12 distally along the guidewire 26 to abrade the tissue and, for example, increase the size of the passage through the body lumen. The practitioner may also move the drive coil 12 proximally along the guidewire 26, and may repetitively move the component in distal and proximal directions to obtain a back-and-forth motion of the tissue-removing element 20 across the tissue. During the process of rotating the tissue-removing element 20, the controller 50 monitors an estimated torque at the drive assembly 48 to prevent any over-torqueing conditions which could damage the catheter 10 or harm the subject. When the practitioner is finished using the catheter 10, the catheter can be withdrawn from the body lumen and unloaded from the guidewire 26 by sliding the catheter proximally along the guidewire. The guidewire 26 used for the abrading process may remain in the body lumen for use in a subsequent procedure.

When introducing elements of the present invention or the one or more embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above apparatuses, systems, and methods without departing from the scope of the invention, it is intended that all matter contained in the above description and shown in the accompanying drawings shall be interpreted as illustrative and not in a limiting sense.

What is claimed is:

1. A tissue-removing catheter for removing tissue in a body lumen, the tissue-removing catheter comprising:
   an elongate body having an axis and proximal and distal end portions spaced apart from one another along the axis, the elongate body being sized and shaped to be received in the body lumen;
   a tissue-removing element mounted on the distal end portion of the elongate body, the tissue-removing element being configured to remove the tissue as the tissue-removing element is rotated by the elongate body within the body lumen;
   a motor operatively engaging the elongate body for driving rotation of the elongate body and tissue-removing element mounted on the elongate body;
   a controller operatively connected to the motor and configured to perform a torque response routine to control a speed of the motor based on a set PWM value of the motor and a detected current applied to the motor during rotation of the elongate body and tissue-removing element; and
   memory in communication with the controller and a motor drivetrain output operatively connected to the motor, a lookup table being stored in the memory for reference by the controller for estimating a torque at the motor drivetrain output.

2. A tissue-removing catheter as set forth in claim 1, further comprising a handle mounted to the proximal end portion of the elongate body, the controller being disposed in the handle.

3. A tissue-removing catheter as set forth in claim 1, further comprising a sensor arranged with respect to motor for measuring the speed of the motor.

4. A tissue-removing catheter as set forth in claim 1, wherein the lookup table is a 2-factor lookup table including a plurality of PWM value/motor current pairs corresponding to a desired PWM value, the controller referencing the 2-factor lookup table to apply the desired PWM value associated with the set PWM value and detected motor current.

5. A tissue-removing catheter as set forth in claim 4, wherein the desired PWM value PWM value corresponds to a desired speed of the motor.

6. A tissue-removing catheter for removing tissue in a body lumen, the tissue-removing catheter comprising:
   an elongate body having an axis and proximal and distal end portions spaced apart from one another along the axis, the elongate body being sized and shaped to be received in the body lumen;
   a tissue-removing element mounted on the distal end portion of the elongate body, the tissue-removing element being configured to remove the tissue as the tissue-removing element is rotated by the elongate body within the body lumen;
   a motor operatively engaging the elongate body for driving rotation of the elongate body and tissue-removing element mounted on the elongate body;
   a controller operatively connected to the motor and configured to perform a torque response routine to control a speed of the motor based on a set PWM value of the motor and a detected current applied to the motor during rotation of the elongate body and tissue-removing element; and
   a motor drivetrain output operatively connected to the motor, wherein the controller is configured to estimate a torque at the motor drivetrain output based on the set PWM value and the detected current applied to the motor during a first mode of operation of the motor, and configured to estimate a torque at the motor drivetrain output based on a single factor of a detected current applied to the motor during a second mode of operation of the motor.

7. A tissue-removing catheter as set forth in claim 6, further comprising memory in communication with the controller, a lookup table being stored in the memory for reference by the controller for estimating the torque at the motor drivetrain output during the first mode of operation, and a threshold value being stored in the memory for reference by the controller for comparing with the estimated torque at the motor drivetrain output during the second mode operation.

8. A tissue-removing catheter as set forth in claim 7, wherein in the first mode of operation the motor is rotated at a rate of at or above a predetermined threshold, and in the second mode of operation the motor is rotated at a rate below the predetermined threshold.

9. A tissue-removing catheter as set forth in claim 7, wherein a second lookup table is stored in the memory for reference by the controller for estimating the torque at the motor drivetrain output during a third mode of operation.

10. A tissue-removing catheter for removing tissue in a body lumen, the tissue-removing catheter comprising:
    an elongate body having an axis and proximal and distal end portions spaced apart from one another along the axis, the elongate body being sized and shaped to be received in the body lumen;
    a tissue-removing element mounted on the distal end portion of the elongate body, the tissue-removing element being configured to remove the tissue as the tissue-removing element is rotated by the elongate body within the body lumen;
    a motor operatively engaging the elongate body for driving rotation of the elongate body and tissue-removing element mounted on the elongate body; and
    a controller operatively connected to the motor and configured to monitor a speed of the motor, the controller deactivating the motor in response to a change in the monitored speed being greater than a predetermined amount for a predetermined period of time, wherein the controller determines the change in the monitored speed by calculating a sum of multiple measured speed changes within the predetermined period of time.

11. A tissue-removing catheter as set forth in claim 10, wherein the controller samples speed measurements at a preset interval.

12. A tissue-removing catheter as set forth in claim 10, wherein the controller deactivates the motor by dynamic braking and thereby rapidly arresting rotation of the motor to rapidly dissipate kinetic energy of the motor as heat and electrical energy through a resistive load.

13. A tissue-removing catheter for removing tissue in a body lumen, the tissue-removing catheter comprising:
    an elongate body having an axis and proximal and distal end portions spaced apart from one another along the axis, the elongate body being sized and shaped to be received in the body lumen;

a tissue-removing element mounted on the distal end portion of the elongate body, the tissue-removing element being configured to remove the tissue as the tissue-removing element is rotated by the elongate body within the body lumen;

a motor assembly including a motor and a motor drivetrain output, the motor assembly operatively engaging the elongate body for driving rotation of the elongate body and tissue-removing element mounted on the elongate body; and a controller operatively connected to the motor and configured to control a speed of the motor, the controller controlling the speed of the motor based on a logistic speed control curve, wherein the logistic speed control curve includes at least two defined sections of motor control whereby the controller performs different speed control functions in each section, and wherein a first section of the logistic speed control curve comprises an open loop section where the speed of the motor is maintained generally at a constant rate, and a second section of the logistic speed control curve comprises a control region where the speed of the motor is controlled based on an estimated torque at the motor drive.

14. A tissue-removing catheter as set forth in claim 13, wherein the logistic curve is based on the equation:

$$RPM = \left(\Theta_1 + \frac{\Theta_2 - \Theta_1}{1 + e^{\left(\frac{T-\Theta_2}{\Theta_4}\right)}}\right)(1000)$$

where T is an estimated torque at the motor drive and $\Theta_1$, $\Theta_2$, $\Theta_3$, and $\Theta_4$ are predetermined calibration values.

15. A tissue-removing catheter as set forth in claim 13, wherein the first section includes an estimated torque range of less than 1.5 mNm.

16. A tissue-removing catheter as set forth in claim 15, wherein the second section includes an estimated torque range of greater than or equal to about 1.5 mNm.

17. A tissue-removing catheter for removing tissue in a body lumen, the tissue-removing catheter comprising:

an elongate body having an axis and proximal and distal end portions spaced apart from one another along the axis, the elongate body being sized and shaped to be received in the body lumen;

a tissue-removing element mounted on the distal end portion of the elongate body, the tissue-removing element being configured to remove the tissue as the tissue-removing element is rotated by the elongate body within the body lumen;

a motor assembly including a motor and a motor drivetrain output, the motor assembly operatively engaging the elongate body for driving rotation of the elongate body and tissue-removing element mounted on the elongate body; and a controller operatively connected to the motor and configured to control a speed of the motor, the controller controlling the speed of the motor based on a logistic speed control curve, wherein the logistic curve is based on the equation:

$$RPM = \left(\Theta_1 + \frac{\Theta_2 - \Theta_1}{1 + e^{\left(\frac{T-\Theta_3}{\Theta_4}\right)}}\right)(1000)$$

where T is an estimated torque at the motor drive and $\Theta_1$, $\Theta_2$, $\Theta_3$, and $\Theta_4$ are predetermined calibration values.

* * * * *